United States Patent
Gore et al.

(10) Patent No.: US 9,340,515 B2
(45) Date of Patent: *May 17, 2016

(54) PURE ERLOTINIB

(71) Applicant: GENERICS [UK] LIMITED, Hertfordshire (GB)

(72) Inventors: Vinayak Govind Gore, Maharashtra (IN); Anilkumar Tripathi, Maharashtra (IN); Madhav Jadhav, Maharashtra (IN)

(73) Assignee: Generics (UK) Limited, Herfordshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/590,519

(22) Filed: Jan. 6, 2015

(65) Prior Publication Data

US 2015/0111847 A1    Apr. 23, 2015

Related U.S. Application Data

(62) Division of application No. 13/811,628, filed as application No. PCT/GB2011/051394 on Jul. 22, 2011, now Pat. No. 8,952,022.

(30) Foreign Application Priority Data

Jul. 23, 2010 (IN) .......................... 2112/MUM/2010

(51) Int. Cl.
  *C07D 239/94* (2006.01)
  *A61K 31/517* (2006.01)
  *A61K 45/06* (2006.01)
  *A61K 31/7068* (2006.01)

(52) U.S. Cl.
  CPC ............ *C07D 239/94* (2013.01); *A61K 31/517* (2013.01); *A61K 31/7068* (2013.01); *A61K 45/06* (2013.01)

(58) Field of Classification Search
  CPC . C07D 239/94; A61K 31/7068; A61K 31/517
  USPC ....................... 514/266.3; 544/284
  See application file for complete search history.

(56) References Cited

U.S. PATENT DOCUMENTS

| 5,747,498 | A | 5/1998 | Schnur et al. |
| 6,476,040 | B1 | 11/2002 | Norris et al. |
| 8,952,022 | B2 * | 2/2015 | Gore et al. ................. 514/266.3 |
| 2004/0162300 | A1 | 8/2004 | Bubendorf et al. |
| 2006/0154941 | A1 | 7/2006 | Huang |
| 2008/0167327 | A1 | 7/2008 | Westheim |
| 2009/0124642 | A1 | 5/2009 | Canavesi et al. |
| 2009/0131665 | A1 | 5/2009 | Gavenda et al. |
| 2009/0306377 | A1 | 12/2009 | Jyothi Prasad et al. |
| 2010/0004449 | A1 | 1/2010 | Gavenda et al. |
| 2010/0094004 | A1 | 4/2010 | Rao et al. |

FOREIGN PATENT DOCUMENTS

| WO | 0134574 A1 | 5/2001 |
| WO | 2007060691 A2 | 5/2007 |
| WO | 2008102369 A1 | 8/2008 |
| WO | 2009002538 A2 | 12/2008 |
| WO | 2009007984 A2 | 1/2009 |
| WO | 2009024989 A2 | 2/2009 |
| WO | 2009625873 | 2/2009 |
| WO | 2010005924 A1 | 1/2010 |
| WO | 2010040212 A1 | 4/2010 |
| WO | 2012028861 A1 | 3/2012 |

OTHER PUBLICATIONS

McMahon et al. (2000).*
Pinedo et al (2000).*
Knesl et al., "Improved Synthesis of Substituted 6,7-Dihydroxy-4-quinazolineamines: Tandutinib, Erlotinib and Gefitinib," Molecules, 11:286-297, (2006).
March, Advanced Organic Chemistry: Reactions, Mechanisms, and Structure, 4th Ed., pp. 250-252, (1992).
Marzaro et al., "A novel approach to quinazolin-4(3H)-one via quinazoline oxidation: an improved synthesis of 4-anilinoquinazolines," Tetrahedron, 66:962-968, (2010).
WIPO Application No. PCT/GB2011/051394, PCT International Preliminary Report on Patentability mailed Jan. 13, 2013.
WIPO Application No. PCT/GB2011/051394, PCT International Search Report mailed Dec. 28, 2011.
WIPO Application No. PCT/GB2011/051394, PCT Written Opinion of the International Searching Authority mailed Dec. 28, 2011.

* cited by examiner

*Primary Examiner* — Paul V Ward

(74) *Attorney, Agent, or Firm* — Lerner, David, Littenberg, Krumholz & Mentlik, LLP

(57) ABSTRACT

The present invention relates to processes for the preparation of erlotinib and salts and polymorphs thereof preparable by said processes, to medical uses of said erlotinib, salts and polymorphs, and to pharmaceutical compositions comprising the same.

18 Claims, No Drawings

PURE ERLOTINIB

CROSS-REFERENCE TO RELATED APPLICATIONS

The present application is a divisional of Ser. No. 13/811,628 filed Apr. 18, 2013, which is a national stage entry of PCT/GB2011/051394 filed Jul. 22, 2011, which claims priority to IN 2112/MUM/2010 filed Jul. 23, 2010.

FIELD OF THE INVENTION

The present invention relates to processes for the preparation of erlotinib and salts and polymorphs thereof, preferably of high purity. The present invention also relates to erlotinib and salts and polymorphs thereof preparable by said processes, to medical uses of said erlotinib, salts and polymorphs, and to pharmaceutical compositions comprising the same.

BACKGROUND OF THE INVENTION

Erlotinib hydrochloride (1), chemically named as N-(3-ethynylphenyl)-6,7-bis-(2-methoxyethoxy)-4-quinazolinamine monohydrochloride, is an inhibitor of oncogenic and proto-oncogenic protein tyrosine kinases, e.g. epidermal growth factor receptor (EGFR). Erlotinib is therefore useful in the treatment of proliferative disorders and is currently marketed for the treatment of lung cancer and pancreatic cancer.

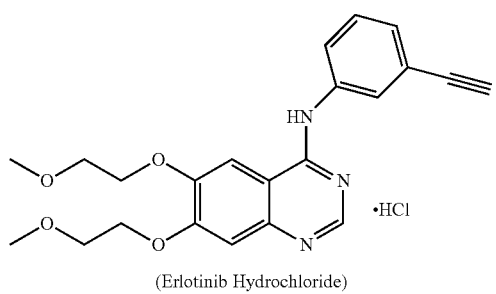

(Erlotinib Hydrochloride)

It has been reported that erlotinib hydrochloride can exist in different polymorphic forms. The manufacturing process for many pharmaceuticals is hindered by the fact that the organic compound which is the active ingredient can exist in more than one polymorphic form. It is essential in pharmaceutical development to ensure that the manufacturing process for the preparation of the active ingredient affords a single polymorph with a consistent level of polymorphic purity. If the manufacturing process produces a product with varying degrees of polymorphic purity and/or or where the process does not control polymorphic inter-conversion, it could lead to serious problems in dissolution and/or bioavailability in the finished pharmaceutical composition comprising the active ingredient.

Erlotinib hydrochloride is disclosed in U.S. Pat. No. 5,747,498 and details of the disclosed method for the preparation of erlotinib hydrochloride are described in Scheme 1.

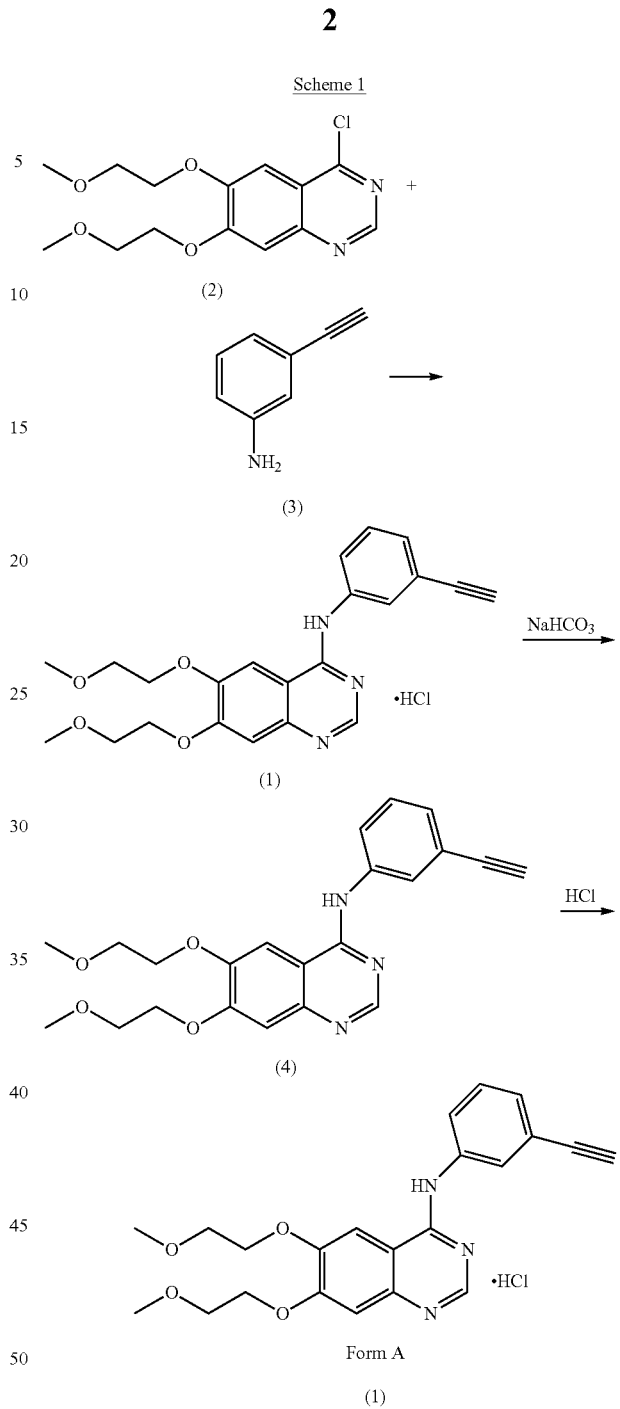

Scheme 1

4-Chloro-6,7-bis-(2-methoxyethoxy)quinazoline (2) was reacted with 3-ethynylaniline (3) or its hydrochloride salt using various solvents and pyridine as a base to yield erlotinib hydrochloride (1) which was treated with a biphasic mixture consisting of saturated aqueous $NaHCO_3$, chloroform and methanol, to form erlotinib base (4). The base (4) obtained in the organic phase was purified by flash chromatography to afford purified erlotinib base. The purified base was further treated with hydrochloric acid in the presence of diethyl ether and chloroform to yield erlotinib hydrochloride. This isolation of purified erlotinib base required the use of a lengthy workup process including column chromatography and required the chlorinated solvent, chloroform, which is not particularly suitable for commercial production of pharmaceuticals. Furthermore, the purification by column chromatography is neither economical not feasible at industrial scale. In addition, substantially pure erlotinib could not be obtained.

Two crystalline forms of erlotinib hydrochloride (polymorph A and polymorph B), were characterized by XRPD in patent application, WO 01/34574. Erlotinib hydrochloride can be obtained in form A or in a mixture of polymorph A and B, by refluxing 3-ethynylaniline and 4-chloro-6,7-bis-(2-methoxyethoxy)-quinazoline in a mixture of toluene and acetonitrile. This afforded polymorph A or a mixture of polymorph A and B. It was also disclosed that the formation of polymorph A was favoured by reducing the amounts of acetonitrile with respect to toluene. Furthermore, erlotinib hydrochloride polymorph A can be converted into polymorph B by refluxing the polymorph A with alcohol/water. Consequently, in the disclosed methods, there was always contamination of form A with form B and vice-versa. In addition, the products of the reaction are not chemically pure and difficult to purify thereafter. Consequently, these methods are not suitable for preparation of commercial quantities of pure polymorph A.

A process for the preparation of erlotinib hydrochloride, polymotph E, by condensation reaction of 3-ethynylaniline and 4-chloro-6,7-bis-(2-methoxyethoxy)quinazoline in (α,α,α)-trifluorotoluene and HCl was disclosed in U.S. Patent application 2004/0162300. Polymorph E was characterized by XRPD, IR and melting point. However, (α,α,α)-trifluotoluene is a highly flammable and dangerous solvent for the environment and is not suitable for commercial production.

A process for the preparation of erlotinib hydrochloride, polymorph A by reaction of erlotinib base with aqueous or gaseous HCl was disclosed in US 2009/0131665. In this method, toluene, a mixture of toluene and methanol, TBME, ethyl acetate, 1-butanol or MIBK were used as a solvent. However, when DCM, diethyl ether, isopropyl acetate, was used as a solvent, polymotph B was formed. In practice, it has been found that the disclosed methods are inconsistent and afford polymorphic mixtures. In particular, example 1 of US 2009/131665 was repeated and erlotinib hydrochloride was obtained with only 97% purity. In addition, XRPD analysis showed that the example afforded form B or mixtures of forms A and B. Furthermore, several crystallizations of erlotinib hydrochloride, obtained from repetition of the example, using various solvents and their combinations would not yield a product pure enough to comply with ICH guidelines.

A process for the preparation of a hydrate of erlotinib hydrochloride comprising crystallization of erlotinib hydrochloride using water as solvent, preferably in the absence of organic solvent was disclosed in US 20080167327. This patent also disclosed the process to prepare hemihydrate polymorph form I as well as form II.

A process for the preparation of erlotinib hydrochloride, polymorph M, N and P by reaction of erlotinib base and aqueous or gaseous HCl dissolved in organic solvents was disclosed in WO 2008/102369.

A process for the preparation of erlotinib hydrochloride by condensation reaction of 4-chloro-6,7-bis-(2-methoxyethoxy)-quinazoline and 3-ethynylaniline in isopropyl alcohol as a solvent and pyridine as a base was disclosed in Molecules Journal (Vol. 11, 286, 2006) but no details on the polymorph were disclosed.

A method for the preparation of erlotinib hydrochloride polymorph A comprising passing hydrochloride gas onto solid erlotinib base containing residual amounts of isopropanol was disclosed in WO 2010/040212. However, in practice it was found that the process did not afford chemically or polymorphically pure product. Repetition of example 1 (page 8) of WO 2010/040212 to prepare erlotinib hydrochloride, by reaction of erlotinib base and gaseous HCl in IPA as a solvent, afforded a mixture of polymorph A and polymorph B (as checked by XRPD).

A process for the preparation of acid salts of erlotinib by reaction of 4-chloro-6,7-bis-(2-methoxyethoxy)-quinazoline and 3-ethynylaniline or an acid salt of 3-ethynylaniline under acidic conditions to form the corresponding erlotinib salt was disclosed in US 2010/0094004. In order to complete the reaction, several hours (6 hours) of reflux was required and hence it is not a cost effective process. In addition, in practice it was found that the process did not afford chemically or polymorphically pure product.

A process for the preparation of erlotinib base, polymorph G1, G2 and G3 was disclosed in WO 2009/002538 and WO 2010/05924.

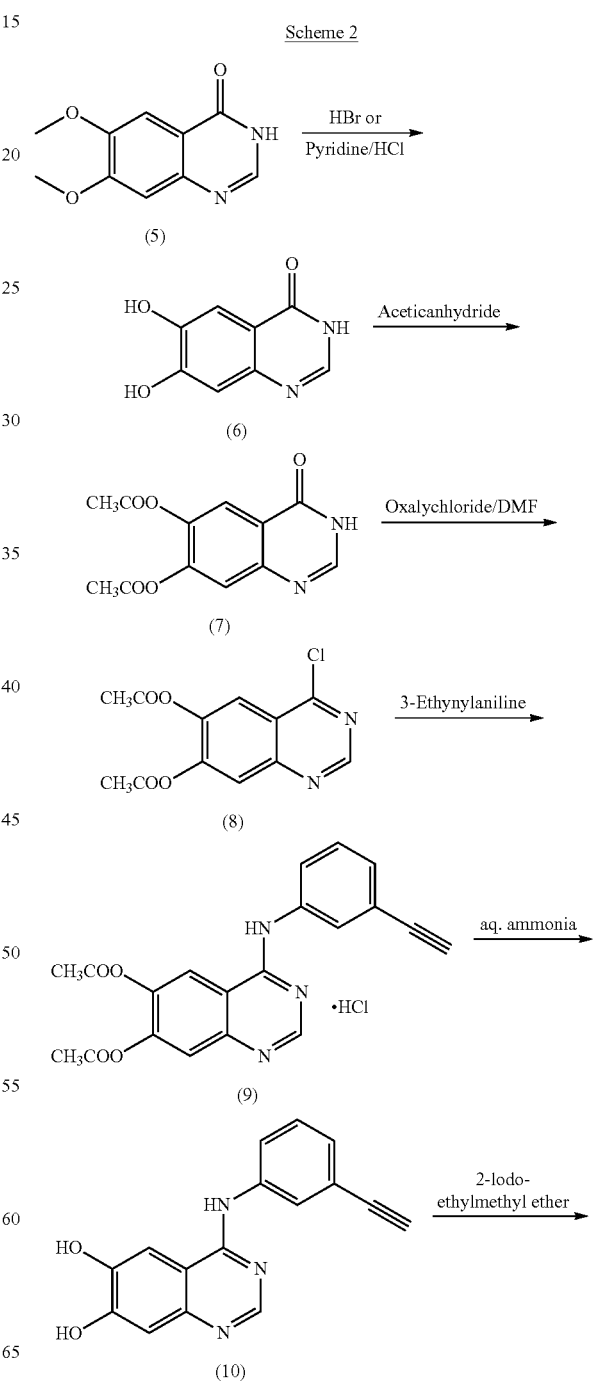

Scheme 2

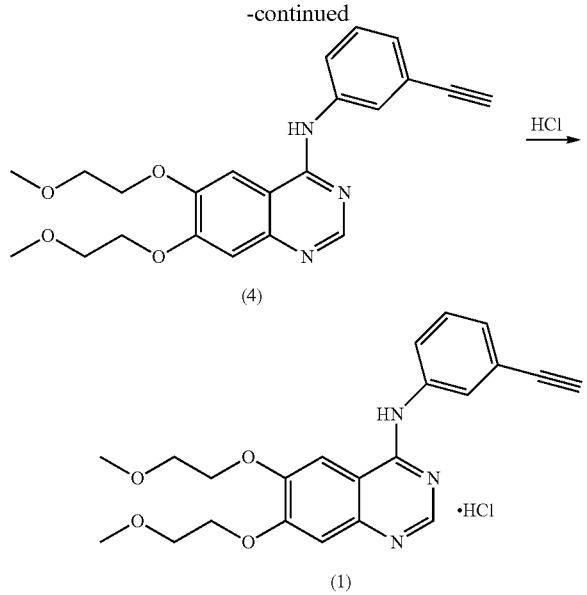

A method for the preparation of erlotinib hydrochloride was disclosed in US 2009/0306377. The method, illustrated in Scheme 2, involves treating 6,7-dimethoxy-4(3H)-quinazolone (5) with hydrobromic acid or pyridine-hydrochloric acid to afford 6,7-dihydroxy-4(3H)-quinazolone (6), which was diacetylated with acetic anhydride to afford diester (7), which was treated with oxalyl chloride/DMF to afford 4-chloro-6,7-diacetoxyquinazoline (8). Compound (8) was condensed with 3-ethynylaniline to afford N-(3-ethynylphenyl)-6,7-dihydroxy-4-quinazolinamine hydrochloride (9), which was converted into the diol N-(3-ethynylphenyl)-6,7-dihydroxy-4-quinazolinamine (10) by treatment with aqueous ammonia/methanol. The diol (10) was treated with 2-iodo-ethylmethyl ether to yield compound (4) which on treatment with HCl afforded erlotinib hydrochloride (1). However, this preparation of erlotinib hydrochloride is a long synthetic route and gives low yields and requires very toxic reagents like pyridine, HBr and controlled reagents like acetic anhydride. Hence, it is not suitable for large scale production.

OBJECT OF THE INVENTION

The prior art processes described above for the preparation of erlotinib and its salts have major disadvantages with respect to the formation and removal of process related chemical and polymorphic impurities; poor commercial viability due to the use of hazardous reactants; expensive, time consuming separation methods such as column chromatography and/or low yields and purity of final and intermediate products.

As the commercial production of erlotinib hydrochloride is of great importance, for the treatment of cancer, and in view of the above disadvantages associated with the prior art there is a real need for alternative and improved processes for the preparation of erlotinib hydrochloride which do not involve multiple steps and further eliminates the need for cumbersome purification techniques, particularly for the removal of the chemical and polymorphic impurities. The alternative processes must be economical and high yielding and provide erlotinib and its salts with a high degree of chemical and polymorphic purity.

Therefore, the objective of the present invention is to develop improved and efficient processes for the preparation of erlotinib base and salts with higher purity and higher yields than in the processes disclosed in the prior art. Another objective is the preparation and purification of erlotinib hydrochloride polymorph A, substantially free from polymorph B and other polymorphs. A further objective is to provide erlotinib and erlotinib hydrochloride free of all chemical and polymorphic impurities.

SUMMARY OF THE INVENTION

The present inventors have surprisingly developed new processes which circumvent the problems associated with the prior art, as described above, which allow the preparation of erlotinib base and its salts, such as the hydrochloride salt, with very high chemical and polymorphic purity.

Therefore a first aspect of the present invention provides a process for the preparation of erlotinib base, or a salt thereof, comprising reacting 4-chloro-6,7-bis-(2-methoxyethoxy)quinazoline and 3-ethynylaniline in a reaction solvent, wherein the reaction mixture does not contain an external acid or base.

As used herein, an "external acid or base" refers to any acid or base other than the 4-chloro-6,7-bis-(2-methoxyethoxy)quinazoline, the 3-ethynylaniline, the reaction solvent, any reaction products thereof and any impurities therein. Preferably the 4-chloro-6,7-bis-(2-methoxyethoxy)quinazoline and/or 3-ethynylaniline are used in their free base form, i.e. not in the form of acid addition salts thereof.

As used herein, an "impurity" refers to any substance present in the reaction mixture in an amount of less than 1% (w/w). Preferably, any impurity is present in the reaction mixture in an amount of less than 0.5% (w/w), less than 0.2% (w/w), or less than 0.1% (w/w). More preferably, any impurity is present in the reaction mixture in an amount of less than 0.05% (w/w), or less than 0.01% (w/w).

In one embodiment of the first aspect of the present invention, an "acid" refers to any compound or ion with a $pK_a$ (relative to water) of less than 0. Optionally, an "acid" refers to any compound or ion with a $pK_a$ of less than 5, or less than 10.

Similarly, a "base" may refer to any compound or ion wherein the conjugate acid of that compound or ion has a $pK_a$ (relative to water) of more than 9. Optionally, the conjugate acid has a $pK_a$ of more than 5, or more than 0.

$pK_a$ values of acids and conjugate acids are known in the art, for example from Table 8.1 on pages 250-2 of "Advanced Organic Chemistry" by J. March, $4^{th}$ Ed., 1992.

In another embodiment of the first aspect of the present invention, the reaction solvent is not an acid or a base.

The reaction solvent may be an apolar solvent, a polar protic solvent, a polar aprotic solvent or a mixture thereof. Preferably the reaction solvent is a polar protic solvent.

In one embodiment of the first aspect of the present invention, the reaction solvent is not 2-propanol.

In another embodiment of the first aspect, the present invention provides a process for the preparation of substantially pure erlotinib base, or a substantially pure salt thereof, comprising reacting 4-chloro-6,7-bis-(2-methoxyethoxy)quinazoline and 3-ethynylaniline in a reaction solvent, wherein the reaction mixture does not contain an external acid or base.

Preferably, the reaction solvent in the first aspect of the present invention is a straight chain, branched or cyclic $C_1$ to $C_6$ alcohol, more preferably, the reaction solvent is selected from methanol, ethanol, propanol, 1-butanol or mixtures thereof. More preferably still the reaction solvent is selected from methanol, ethanol, or mixtures thereof, and most preferably, the reaction solvent is methanol.

As used herein, a "straight chain, branched or cyclic alcohol" refers to any straight chain, branched or cyclic hydrocarbon that is substituted with at least one hydroxyl group. Optionally said hydrocarbon may be further substituted.

Preferably the "straight chain, branched or cyclic alcohol" is $R^1OH$, wherein $R^1$ is selected from an optionally substituted alkyl, alkenyl, alkynyl, aryl, arylalkyl, arylalkenyl, arylalkynyl, alkylaryl, alkenylaryl or alkynylaryl group. Preferably $R^1$ is an optionally substituted alkyl or arylalkyl group. More preferably $R^1$ is an optionally substituted $C_1$ to $C_{20}$ alkyl group, more preferably still $R^1$ is an optionally substituted $C_1$ to $C_{12}$ alkyl group. Preferably $R^1OH$ is monohydric.

For the purposes of the present invention, an "alkyl" group is defined as a monovalent saturated hydrocarbon, which may be straight-chained or branched, or be or include cyclic groups. An alkyl group may optionally include one or more heteroatoms N, O or S in its carbon skeleton. Examples of alkyl groups are methyl, ethyl, ii-propyl, i-propyl, i-butyl, t-butyl and n-pentyl groups. Preferably an alkyl group is straight-chained or branched and does not include any heteroatoms in its carbon skeleton. Preferably an alkyl group is a $C_1$-$C_{12}$ alkyl group, which is defined as an alkyl group containing from 1 to 12 carbon atoms. More preferably an alkyl group is a $C_1$-$C_6$ alkyl group, which is defined as an alkyl group containing from 1 to 6 carbon atoms. An "alkylene" group is similarly defined as a divalent alkyl group.

An "alkenyl" group is defined as a monovalent hydrocarbon, which comprises at least one carbon-carbon double bond, which may be straight-chained or branched, or be or include cyclic groups. An alkenyl group may optionally include one or more heteroatoms N, O or S in its carbon skeleton. Examples of alkenyl groups are vinyl, allyl, but-1-enyl and but-2-enyl groups. Preferably an alkenyl group is straight-chained or branched and does not include any heteroatoms in its carbon skeleton. Preferably an alkenyl group is a $C_2$-$C_{12}$ alkenyl group, which is defined as an alkenyl group containing from 2 to 12 carbon atoms. More preferably an alkenyl group is a $C_2$-$C_6$ alkenyl group, which is defined as an alkenyl group containing from 2 to 6 carbon atoms. An "alkenylene" group is similarly defined as a divalent alkenyl group.

An "alkynyl" group is defined as a monovalent hydrocarbon, which comprises at least one carbon-carbon triple bond, which may be straight-chained or branched, or be or include cyclic groups. An alkynyl group may optionally include one or mote heteroatoms N, O or S in its carbon skeleton. Examples of alkynyl groups are ethynyl, propargyl, but-1-ynyl and but-2-ynyl groups. Preferably an alkynyl group is straight-chained or branched and does not include any heteroatoms in its carbon skeleton. Preferably an alkynyl group is a $C_2$-$C_{12}$ alkynyl group, which is defined as an alkynyl group containing from 2 to 12 carbon atoms. More preferably an alkynyl group is a $C_2$-$C_6$ alkynyl group, which is defined as an alkynyl group containing from 2 to 6 carbon atoms. An "alkynylene" group is similarly defined as a divalent alkynyl group.

An "aryl" group is defined as a monovalent aromatic hydrocarbon. An aryl group may optionally include one or more heteroatoms N, O or S in its carbon skeleton. Examples of aryl groups are phenyl, naphthyl, anthracenyl and phenanthrenyl groups. Preferably an aryl group does not include any heteroatoms in its carbon skeleton. Preferably an aryl group is a $C_4$-$C_{14}$ aryl group, which is defined as an aryl group containing from 4 to 14 carbon atoms. More preferably an aryl group is a $C_6$-$C_{10}$ aryl group, which is defined as an aryl group containing from 6 to 10 carbon atoms. An "arylene" group is similarly defined as a divalent aryl group.

For the purposes of the present invention, where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

For the purposes of this invention, an optionally substituted alkyl, alkenyl, alkynyl, aryl, arylalkyl, arylalkenyl, arylalkynyl, alkylaryl, alkenylaryl, alkynylaryl or hydrocarbyl group may be substituted with one or more of —F, —Cl, —Br, —I, —$CF_3$, —$CCl_3$, —$CBr_3$, —$CI_3$, —OH, —SH, —$NH_2$, —CN, —$NO_2$, —$N_3$, —COOH, —$R^\alpha$—O—$R^\beta$, —$R^\alpha$—S—$R^\beta$, —$R^\alpha$—SO—$R^\beta$, —$R^\alpha$—$SO_2$—$R^\beta$, —$R^\alpha$—$SO_2$—$OR^\beta$, —$R^\alpha O$—$SO_2$—$R^\beta$, —$R^\alpha$—$SO_2$—$N(R^\beta)_2$, —$R^\alpha$—$NR^\beta$—$SO_2$—$R^\beta$, —$R^\alpha O$—$SO_2$—$OR^\beta$, —$R^\alpha O$—$SO_2$—$N(R^\beta)_2$, —$R^\alpha$—$NR^\beta$—$SO_2$—$OR^\beta$, —$R^\alpha$—$NR^\beta$—$SO_2$—$N(R^\beta)_2$, —$R^\alpha$—$N(R^\beta)_2$, —$R^\alpha$—$N(R^\beta)_3^+$, —$R^\alpha$—$P(R^\beta)_2$, —$R^\alpha$—Si$(R^\beta)_3$, —$R^\alpha$—CO—$R^\beta$, —$R^\alpha$—CO—$OR^\beta$, —$R^\alpha O$—CO—$R^\beta$, —$R^\alpha$—CO—$N(R^\beta)_2$, —$R^\alpha$—$NR^\beta$—CO—$R^\beta$, —$R^\alpha O$—CO—$OR^\beta$, —$R^\alpha O$—CO—$N(R\beta)_2$, —$R^\alpha$—$NR^\beta$—CO—$OR^\beta$, —$R^\alpha$—$NR^\beta$—CO—$N(R^\beta)_2$, —$R^\alpha$—CS—$R^\beta$, —$R^\alpha$—CS—$OR^\beta$, —$R^\alpha$—$NR^\beta$—CS—$OR^\beta$, —$R^\alpha$—$NR^\beta$—CS—$N(R^\beta)_2$, —$R^\beta$, a bridging substituent such as —O—, —S—, —$NR^\beta$— or —$R^\alpha$—, or a π-bonded substituent such as =O, =S or =$NR^\beta$. In this context, —$R^\alpha$— is independently a chemical bond, a $C_1$-$C_{10}$ alkylene, $C_1$-$C_{10}$ alkenylene or $C_1$-$C_{10}$ alkynylene group. —$R^\beta$ is independently hydrogen, unsubstituted $C_1$-$C_6$ alkyl or unsubstituted $C_6$-$C_{10}$ aryl. Optional substituent(s) are preferably taken into account when calculating the total number of carbon atoms in the parent group substituted with the optional substituent(s). Preferably an optionally substituted alkyl, alkenyl, alkynyl, aryl, arylalkyl, arylalkenyl, arylalkynyl, alkylaryl, alkenylaryl or alkynylaryl group is not substituted with a bridging substituent. Preferably an optionally substituted alkyl, alkenyl, alkynyl, aryl, arylalkyl, arylalkenyl, arylalkynyl, alkylaryl, alkenylaryl or alkynylaryl group is not substituted with a π-bonded substituent. Preferably a substituted group comprises 1, 2 or 3 substituents, more preferably 1 or 2 substituents, and even more preferably 1 substituent.

Any optional substituent may be protected. Suitable protecting groups for protecting optional substituents are known in the art, for example from "Protective Groups in Organic Synthesis" by T. W. Greene and P. G. M. Wuts (Wiley-Interscience, 4$^{th}$ edition, 2006).

In a preferred embodiment of the first aspect of the present invention, the reaction mixture consists of:
  (a) 4-chloro-6,7-bis-(2-methoxyethoxy)quinazoline;
  (b) 3-ethynylaniline;
  (c) a reaction solvent selected from methanol, ethanol and mixtures thereof; and
  (d) any reaction products and impurities thereof.

More preferably still, the reaction mixture consists of:
  (a) 4-chloro-6,7-bis-(2-methoxyethoxy)quinazoline;
  (b) 3-ethynylaniline;
  (c) methanol; and
  (d) any reaction products and impurities thereof.

In one embodiment of the first aspect of the present invention, from 1 to 100 volumes of the reaction solvent are used, i.e. for every 1 g of 4-chloro-6,7-bis-(2-methoxyethoxy)-quinazoline starting material, from 1 to 100 ml of the reaction solvent are used. Preferably from 5 to 50 volumes of the reaction solvent are used, more preferably from 10 to 30 volumes. Most preferably about 20 volumes of the reaction solvent are used.

In another embodiment of the first aspect of the present invention, from 0.5 to 5 equivalents of 3-ethynylaniline are used, relative to the 4-chloro-6,7-bis-(2-methoxyethoxy) quinazoline. Preferably from 1 to 2 equivalents of 3-ethynylaniline are used, more preferably from 1.05 to 1.50 equivalents. Most preferably about 1.1 equivalents of 3-ethynylaniline are used.

Preferably, the reaction mixture is heated in the process according to the first aspect of the present invention. Preferably, the reaction mixture is heated at about the reflux temperature of the reaction solvent or alternatively, the reaction mixture is heated at 35-40° C.

In one embodiment, the reaction mixture may be heated for between 10 minutes and 48 hours. Preferably the reaction mixture is heated for between 30 minutes and 24 hours, more preferably for between 1 hour and 12 hours, and most preferably for between 2 hours and 4 hours.

In one embodiment, the reaction mixture is heated to a first temperature of 35-40° C. for a first period of time and then is heated to about the reflux temperature of the solvent for a second period of time. Preferably the first period of time is from 5 to 60 minutes, more preferably from 10 to 30 minutes and most preferably about 15 minutes. Preferably the second period of time is from 30 minutes to 24 hours, more preferably from 1 hour to 12 hours, and most preferably from 2 hours to 3 hours.

Preferably, in the process according to the first aspect of the present invention, the salt of erlotinib is the hydrochloride salt.

In a preferred embodiment of the first aspect of the present invention, erlotinib hydrochloride is crystallised and/or isolated from the reaction mixture.

Optionally, the process of the first aspect of the present invention further comprises the step of treating a salt of erlotinib with a base to yield erlotinib base. Preferably the salt of erlotinib is erlotinib hydrochloride, which may optionally have been crystallised and/or isolated from the reaction mixture.

The base may be an organic base such as an amine, or an inorganic base such as ammonia, a hydroxide, a carbonate or a bicarbonate. Preferably the base is a carbonate or a bicarbonate. More preferably the base is a metal or ammonium carbonate or bicarbonate, such as sodium carbonate, sodium bicarbonate, potassium carbonate, potassium bicarbonate, ammonium carbonate or ammonium bicarbonate. Most preferably the base is sodium carbonate.

Typically, from 1 to 10 equivalents of base may be used, relative to the salt of erlotinib. Preferably from 1.5 to 5 equivalents of base are used, and most preferably about 2 equivalents of base are used.

In one embodiment of the first aspect of the present invention, the step of treating a salt of erlotinib with a base to yield erlotinib base may be performed in the reaction solvent. Alternatively, a separate solvent may be used. In either case, the salt of erlotinib may be suspended in the solvent or dissolved in the solvent. Preferably the salt of erlotinib is suspended in the solvent.

Where a separate solvent is used, the solvent may be selected from an apolar solvent, a polar protic solvent, a polar aprotic solvent, or a mixture thereof. Preferably the solvent is a polar protic solvent such as water or a straight chain, branched or cyclic alcohol, or a mixture thereof. The straight chain, branched or cyclic alcohol may be a $C_1$-$C_{20}$ alcohol. Preferably the alcohol is a $C_1$-$C_{12}$ alcohol, more preferably a $C_1$-$C_6$ alcohol such as methanol, ethanol, 1-propanol, 2-propanol, 1-butanol, 2-methyl-1-propanol, t-butanol, 1-pentanol, cyclopentanol, 1-hexanol, cyclohexanol, or a mixture thereof.

In a preferred embodiment of the first aspect of the present invention, the step of treating a salt of erlotinib with a base to yield erlotinib base is performed in a solvent comprising methanol and/or ethanol. Optionally said solvent further comprises water.

In a particularly preferred embodiment, the step of treating a salt of erlotinib with a base to yield erlotinib base is performed in a solvent consisting of (a) methanol and/or ethanol, and (b) optionally water.

Most preferably, the step of treating a salt of erlotinib with a base to yield erlotinib base is performed in a water and methanol mixture.

Where the step of treating a salt of erlotinib with a base to yield erlotinib base is performed in a solvent comprising a mixture of water and a straight chain, branched or cyclic alcohol, it is preferred that the water and the alcohol are present in a ratio of from 1:19 to 19:1 by volume. More preferably the water and the alcohol are present in a ratio of from 1:3 to 3:1 by volume. Most preferably the water and the alcohol are present in a ratio of about 1:1 by volume.

In one embodiment of the first aspect of the present invention, from 1 to 100 volumes of solvent are used for the step of treating a salt of erlotinib with a base to yield erlotinib base, i.e. for every 1 g of the salt of erlotinib, from 1 to 100 ml of solvent are used. Preferably from 5 to 50 volumes of solvent are used, more preferably from 10 to 30 volumes. Most preferably about 20 volumes of solvent are used.

In another embodiment of the first aspect of the present invention, the step of treating a salt of erlotinib with a base to yield erlotinib base is performed at a temperature of from 0 to 100° C. Preferably the step is performed at a temperature of from 10 to 50° C. Most preferably the step is performed at a temperature of from 25 to 30° C.

Typically, the step of treating a salt of erlotinib with a base to yield erlotinib base may be performed over a period of time from 15 minutes to 24 hours, more preferably from 30 minutes to 6 hours, and most preferably over a period of about 2 hours.

Preferably, erlotinib base is isolated in the process according to the first aspect of the present invention. Fat instance, the erlotinib base may be isolated by crystallisation from the solvent in which the step of treating a salt of erlotinib with a base to yield erlotinib base is performed.

Preferably, the isolated erlotinib base is further purified, typically by crystallization from a solvent, wherein the solvent is preferably a straight chain, branched or cyclic $C_1$ to $C_6$ alcohol, wherein the solvent is more preferably selected from methanol, ethanol, propanol, 1-butanol or mixtures thereof and most preferably, the solvent is 1-butanol.

Alternatively, the isolated erlotinib base may be further purified by crystallisation from a solvent wherein the solvent is a straight chain, branched or cyclic $C_4$ to $C_{20}$ alcohol. Preferably the solvent is a straight chain, branched or cyclic $C_4$ to $C_{12}$ alcohol, or $C_4$ to $C_8$ alcohol such as 1-butanol, 2-methyl-1-propanol, t-butanol, 1-pentanol, cyclopentanol, 1-hexanol, cyclohexanol, 1-heptanol, 1-octanol, or a mixture thereof. Most preferably the solvent is 1-butanol.

Where the isolated erlotinib base is further purified by crystallization from a solvent, the crystallisation may optionally be performed by heating the isolated erlotinib base in the solvent at a first temperature until the erlotinib base has dissolved, and then cooling the solution to a second temperature to allow the purified erlotinib base to crystallise. Preferably the first temperature is from 60 to 100° C., and more preferably from 80 to 90° C. Preferably the second temperature is from −10 to 40° C., and more preferably from 25 to 30° C.

Optionally, the isolated erlotinib base is dissolved in the solvent and treated with activated charcoal, also known as activated carbon, prior to crystallisation from the solvent.

Preferably, wherein the isolated erlotinib base is further purified by crystallisation from a solvent, between 1 and 20 volumes of solvent are used, i.e. for every 1 g of isolated erlotinib base, from 1 to 20 ml of solvent are used. More preferably between 3 and 15 volumes of solvent are used. Most preferably between 6 and 8 volumes of solvent are used.

Preferably, the crude erlotinib base is purified by dissolving in 1-butanol, optionally with activated charcoal, at a temperature between 65° C. and 100° C., more preferably wherein the temperature is between 80-90° C.

A preferred process according to the first aspect of the present invention is when the isolated erlotinib base, which is optionally further purified as described above, is converted into erlotinib hydrochloride by reaction in a solvent with aqueous HCl or non-aqueous HCl. Preferably, the solvent is a straight chain, branched or cyclic $C_1$ to $C_6$ alcohol, more preferably, the solvent is selected from methanol, ethanol, propanol, 1-butanol, 1-pentanol or mixtures thereof and most preferably the solvent is 1-pentanol.

Alternatively the isolated erlotinib base, which is optionally further purified as described above, may be converted into erlotinib hydrochloride by reaction in a solvent with aqueous HCl or non-aqueous HCl, wherein the solvent is a straight chain, branched or cyclic $C_5$ to $C_{20}$ alcohol. Preferably the solvent is a straight chain, branched or cyclic $C_5$ to $C_{12}$ alcohol, or $C_5$ to $C_8$ alcohol such as 1-pentanol, cyclopentanol, 1-hexanol, cyclohexanol, 1-heptanol, 1-octanol or mixtures thereof. Most preferably the solvent is 1-pentanol.

Where the isolated erlotinib base is converted into erlotinib hydrochloride by reaction in a solvent with aqueous HCl or non-aqueous HCl, preferably from 1 to 100 volumes of solvent are used, i.e. for every 1 g of erlotinib base, from 1 to 100 ml of solvent are used. Preferably from 5 to 50 volumes of solvent are used, more preferably from 10 to 30 volumes. Most preferably about 20 volumes of solvent are used. Preferably the erlotinib hydrochloride crystallises from the solvent.

In one embodiment, where aqueous HCl is used, the isolated erlotinib base is converted into erlotinib hydrochloride at a temperature of from −10 to 40° C., more preferably from 0 to 30° C., and most preferably from 5 to 10° C.

Where aqueous HCl is used, it is preferred that the concentration of the aqueous HCl is from 10 to 50% (w/w). More preferably, the concentration is from 20 to 40% (w/w), more preferably still from 30 to 38% (w/w). Most preferably, the concentration is about 35% (w/w).

In another embodiment, where non-aqueous HCl is used, the erlotinib base is converted into erlotinib hydrochloride at a temperature of from −10 to 40° C., more preferably from 0 to 30° C., and most preferably from 20 to 25° C.

Where non-aqueous HCl is used, it may be used as a gas, or as a non-aqueous solution. Preferably, the non-aqueous HCl is a non-aqueous solution, such as a solution of HCl in a straight chain, branched or cyclic alcohol. Optionally, the same solvent is used for dissolving the HCl as is used for the conversion of erlotinib base into erlotinib hydrochloride.

Where HCl is dissolved in a non-aqueous solvent, typically the concentration of the HCl in the non-aqueous solvent may be from 1 to 50% (w/w). Preferably, the concentration is from 10 to 30% (w/w), more preferably from 15 to 20% (w/w). Most preferably, the concentration is from 16 to 18% (w/w).

Preferably the isolated erlotinib base is converted into erlotinib hydrochloride by reaction in a solvent with aqueous HCl or non-aqueous HCl over a period of from 5 minutes to 24 hours, more preferably from 15 minutes to 6 hours, more preferably still from 30 minutes to 3 hours and most preferably for a period of about 1 hour.

Preferably, the erlotinib hydrochloride obtained by the process according to the first aspect of the present invention is further purified by crystallization from a solvent. Preferably, the solvent is a straight chain, branched or cyclic $C_1$ to $C_6$ alcohol, more preferably, the solvent is selected from methanol, ethanol, propanol, 1-butanol, 1-pentanol or mixtures thereof and most preferably, the solvent is 1-pentanol.

Alternatively the erlotinib hydrochloride obtained by the process according to the first aspect of the present invention is further purified by crystallization from a solvent selected from a straight chain, branched or cyclic $C_5$ to $C_{20}$ alcohol. Preferably the solvent is a straight chain, branched or cyclic $C_5$ to $C_{12}$ alcohol, or $C_5$ to $C_8$ alcohol such as 1-pentanol, cyclopentanol, 1-hexanol, cyclohexanol, 1-heptanol, 1-octanol or mixtures thereof. Most preferably the solvent is 1-pentanol.

Where the erlotinib hydrochloride is further purified by crystallization from a solvent, preferably from 1 to 100 volumes of solvent are used, i.e. for every 1 g of erlotinib hydrochloride, from 1 to 100 ml of solvent are used. Preferably from 5 to 50 volumes of solvent are used, more preferably from 10 to 30 volumes. Most preferably about 20 volumes of solvent are used.

In one embodiment, the erlotinib hydrochloride is further purified by crystallization from a solvent at a temperature of from −10 to 40° C., more preferably from 0 to 30° C., and most preferably from 5 to 10° C.

In another embodiment, the erlotinib hydrochloride is further purified by crystallization from a solvent at a temperature of from 20 to 25° C.

Preferably, the erlotinib hydrochloride is isolated as the form A polymorph.

As used herein, the "form A" polymorph of erlotinib hydrochloride refers to the polymorphic form which exhibits an X-ray powder diffraction (XRPD) pattern comprising at least three characteristic peaks selected from 5.6, 6.2, 7.5, 8.0, 8.7, 9.8, 11.3, 13.3, 15.1, 15.5, 16.2, 17.0, 18.4, 18.9, 19.5, 21.2, 21.3, 22.4, 22.7, 23.5, 24.2, 24.6, 25.4, 26.2, 26.6, 27.1, 29.2, 30.0, 30.7, 32.8, 34.4, 36.2, 37.4 and 38.9±0.2 degrees 2θ, as measured using a Cu anode, $K\alpha_1$=1.54056 Å and $K\alpha_2$=1.54439 Å. Thus, for instance, form A may exhibit an X-ray powder diffraction pattern comprising at least the characteristic peaks 5.6, 9.8, 18.9, 22.7 and 23.5±0.2 degrees 2θ.

Preferably form A exhibits an X-ray powder diffraction pattern comprising at least four, at least five, at least ten, or all 34 characteristic peaks selected from 5.6, 6.2, 7.5, 8.0, 8.7, 9.8, 11.3, 13.3, 15.1, 15.5, 16.2, 17.0, 18.4, 18.9, 19.5, 21.2, 21.3, 22.4, 22.7, 23.5, 24.2, 24.6, 25.4, 26.2, 26.6, 27.1, 29.2, 30.0, 30.7, 32.8, 34.4, 36.2, 37.4 and 38.9±0.2 degrees 2θ.

Accordingly, as used herein, "form A" is substantially as described in WO 01/34574, albeit optionally in a higher degree of purity.

A second aspect of the present invention provides a process for the preparation of erlotinib base, comprising reacting a salt of erlotinib with a base in a solvent consisting of:
(a) methanol and/or ethanol; and
(b) optionally water.

In one embodiment of the second aspect of the present invention, the base may be an organic base such as an amine, or an inorganic base such as ammonia, a hydroxide, a carbonate or a bicarbonate. Preferably the base is a carbonate or a bicarbonate.

A third aspect of the present invention provides a process for the preparation of erlotinib base, comprising reacting a salt of erlotinib with a carbonate or bicarbonate base in a solvent consisting of one or more polar protic solvents.

In one embodiment of the third aspect of the present invention, the solvent may consist of water or a straight chain, branched or cyclic alcohol, or a mixture thereof.

Preferably the straight chain, branched or cyclic alcohol is a $C_1$-$C_{20}$ alcohol. More preferably the alcohol is a $C_1$-$C_{12}$ alcohol, more preferably still a $C_1$-$C_6$ alcohol such as methanol, ethanol, 1-propanol, 2-propanol, 1-butanol, 2-methyl-1-propanol, t-butanol, 1-pentanol, cyclopentanol, 1-hexanol, cyclohexanol, or a mixture thereof. Most preferably the straight chain, branched or cyclic alcohol is methanol and/or ethanol.

In a preferred embodiment of either of the second or third aspects of the present invention, the solvent consists of water and methanol.

In either of the second or third aspects of the present invention, the salt of erlotinib may be suspended in the solvent or dissolved in the solvent. Preferably the salt of erlotinib is suspended in the solvent.

In a preferred embodiment of either the second or third aspects of the present invention, the salt of erlotinib is erlotinib hydrochloride.

Optionally the salt of erlotinib is prepared by a process according to the first aspect of the present invention. In one embodiment of the second or third aspects of the present invention, the solvent is the same as the reaction solvent used in the first aspect of the present invention. Alternatively, a separate solvent may be used.

Where the base used in accordance with the second or third aspect of the present invention is a carbonate or a bicarbonate, preferably the base is a metal or ammonium carbonate or bicarbonate, such as sodium carbonate, sodium bicarbonate, potassium carbonate, potassium bicarbonate, ammonium carbonate or ammonium bicarbonate. Most preferably the base is sodium carbonate.

Typically, from 1 to 10 equivalents of base may be used, relative to the salt of erlotinib. Preferably from 1.5 to 5 equivalents of base are used, and most preferably about 2 equivalents of base are used.

Where the process of the second or third aspect of the present invention is performed in a solvent consisting of a mixture of water and a straight chain, branched or cyclic alcohol, it is preferred that the water and the alcohol are present in a ratio of from 1:19 to 19:1 by volume. More preferably the water and the alcohol are present in a ratio of from 1:3 to 3:1 by volume. Most preferably the water and the alcohol are present in a ratio of about 1:1 by volume.

In one embodiment of the second or third aspect of the present invention, from 1 to 100 volumes of solvent are used, i.e. for every 1 g of the salt of erlotinib, from 1 to 100 ml of solvent are used. Preferably from 5 to 50 volumes of solvent are used, more preferably from 10 to 30 volumes. Most preferably about 20 volumes of solvent are used.

In another embodiment of the second or third aspect of the present invention, the process is performed at a temperature of from 0 to 100° C. Preferably the process is performed at a temperature of from 10 to 50° C. Most preferably the process is performed at a temperature of from 25 to 30° C.

Typically, the process of the second or third aspect of the present invention may be performed over a period of from 15 minutes to 24 hours, more preferably from 30 minutes to 6 hours, and most preferably over a period of about 2 hours.

Preferably, the erlotinib base is isolated following the process according to the second or third aspect of the present invention. For instance, the erlotinib base may be isolated by crystallisation from the solvent.

A fourth aspect of the present invention provides a process for the preparation of erlotinib base, comprising the crystallisation of erlotinib base from a solvent comprising a straight chain, branched or cyclic $C_4$ to $C_{20}$ alcohol.

Preferably the process of the fourth aspect of the present invention purifies the erlotinib base.

The erlotinib base used in the fourth aspect of the present invention may optionally be prepared by a process according to any of the first to third aspects of the present invention.

In one embodiment of the fourth aspect of the present invention, the solvent is a straight chain, branched or cyclic $C_4$ to $C_{12}$ alcohol, or $C_4$ to $C_8$ alcohol such as 1-butanol, 2-methyl-1-propanol, t-butanol, 1-pentanol, cyclopentanol, 1-hexanol, cyclohexanol, 1-heptanol or 1-octanol. Preferably the solvent is 1-butanol.

In another embodiment of the fourth aspect of the present invention, the crystallisation may be performed by heating the erlotinib base in the solvent at a first temperature until the erlotinib base has dissolved, and then cooling the solution to a second temperature to allow the purified erlotinib base to crystallise. Preferably the first temperature is from 60 to 100° C., and more preferably from 80 to 90° C. Preferably the second temperature is from 10 to 40° C., and more preferably from 25 to 30° C.

Optionally, the erlotinib base is dissolved in the solvent and treated with activated charcoal, also known as activated carbon, prior to crystallisation from the solvent.

In another embodiment of the fourth aspect of the present invention, between 1 and 20 volumes of solvent are used for the crystallisation, i.e. for every 1 g of erlotinib base, from 1 to 20 ml of solvent are used. More preferably between 3 and 15 volumes of solvent are used. Most preferably between 6 and 8 volumes of solvent are used.

In a preferred embodiment of the fourth aspect of the present invention, erlotinib base is purified by dissolving in 1-butanol, optionally with activated charcoal, at a temperature between 65° C. and 100° C., more preferably wherein the temperature is between 80-90° C.

In any of the first to fourth aspects of the present invention, the erlotinib base or salt thereof may be substantially pure.

In one embodiment of any of the first to fourth aspects of the present invention, the HPLC purity of the erlotinib base or salt obtained is more than 97%, more preferably more than 98%, more preferably more than 99%, more preferably more than 99.5%, more preferably more than 99.8% and most preferably more than 99.9%. Preferably, the salt obtained is the hydrochloride.

As used herein, the percentage HPLC purity is measured by the area normalisation method.

Where erlotinib base is isolated, it may in one embodiment be isolated as a hydrate. Preferably said hydrate has a water content of ≤5% (w/w).

In another embodiment, where erlotinib base is isolated, it may be isolated as an anhydrate. Preferably said anhydrate has a water content of ≤0.5% (w/w). More preferably, said anhydrate has a water content of ≤0.2% (w/w).

A fifth aspect of the present invention provides erlotinib base or a salt thereof with a HPLC purity of more than 99.0%, more preferably more than 99.5%, more preferably more than 99.8% and most preferably more than 99.9%. Preferably, in the fifth aspect of the present invention the salt is the hydrochloride.

In one embodiment of the fifth aspect of the present invention, erlotinib base with a HPLC purity of ≥99.80% is provided. More preferably erlotinib base with a HPLC purity of ≥99.85% is provided, and most preferably erlotinib base with a HPLC purity of ≥99.90% is provided.

The erlotinib base of the fifth aspect of the present invention may optionally be a hydrate. Preferably said hydrate has a water content of ≤5% (w/w).

Alternatively, the erlotinib base of the fifth aspect of the present invention may optionally be an anhydrate. Preferably said anhydrate has a water content of ≤0.5% (w/w). More preferably, said anhydrate has a water content of ≤0.2% (w/w).

In another embodiment of the fifth aspect of the present invention, erlotinib hydrochloride with a HPLC purity of ≥99.85% is provided. More preferably erlotinib hydrochloride with a HPLC purity of ≥99.90% is provided.

A sixth aspect of the present invention provides a process for the preparation of erlotinib hydrochloride form A, comprising crystallization of erlotinib hydrochloride from a solvent.

Optionally, the erlotinib hydrochloride may be prepared by a process according to the first aspect of the present invention, and/or be erlotinib hydrochloride according to the fifth aspect of the present invention.

A seventh aspect of the present invention provides a process for the preparation of erlotinib hydrochloride form A, comprising dissolving erlotinib base in a solvent and mixing with aqueous or non-aqueous HCl and crystallization of erlotinib hydrochloride from the solvent.

Optionally, the erlotinib base may be prepared by a process according to any of the first to fourth aspects of the present invention, and/or be erlotinib base according to the fifth aspect of the present invention.

In one embodiment of the seventh aspect of the present invention, where aqueous HCl is used, the erlotinib base is converted into erlotinib hydrochloride at a temperature of from −10 to 40° C., more preferably from 0 to 30° C., and most preferably from 5 to 10° C.

Where aqueous HCl is used, it is preferred that the concentration of the aqueous HCl is from 10 to 50% (w/w). More preferably, the concentration is from 20 to 40% (w/w), more preferably still from 30 to 38% (w/w). Most preferably, the concentration is about 35% (w/w).

In another embodiment of the seventh aspect of the present invention, where non-aqueous HCl is used, the erlotinib base is converted into erlotinib hydrochloride at a temperature of from −10 to 40° C., more preferably from 0 to 30° C., and most preferably from 20 to 25° C.

Where non-aqueous HCl is used, it may be used as a gas, or as a non-aqueous solution. Preferably, the non-aqueous HCl is a non-aqueous solution, such as a solution of HCl in a straight chain, branched or cyclic alcohol. Optionally, the same solvent as used for dissolving the HCl as is used for dissolving the erlotinib base.

In one embodiment of the seventh aspect of the present invention, where HCl is dissolved in a non-aqueous solvent, the concentration of the HCl is from 1 to 50% (w/w). Preferably, the concentration is from 10 to 30% (w/w), mote preferably from 15 to 20% (w/w). Most preferably, the concentration is from 16 to 18% (w/w).

Preferably the erlotinib base is allowed to react with the aqueous HCl or non-aqueous HCl over a period of from 5 minutes to 24 hours, more preferably from 15 minutes to 6 hours, more preferably still from 30 minutes to 3 hours and most preferably for a period of about 1 hour.

In one embodiment of the sixth or seventh aspects of the present invention, the solvent is a straight chain, branched or cyclic $C_1$ to $C_6$ alcohol, preferably selected from methanol, ethanol, propanol, 1-butanol, 1-pentanol or mixtures thereof. Most preferably the solvent is 1-pentanol.

Alternatively the solvent may be a straight chain, branched or cyclic $C_5$ to $C_{20}$ alcohol. Preferably the solvent is a straight chain, branched or cyclic $C_5$ to $C_{12}$ alcohol, or $C_5$ to $C_8$ alcohol such as 1-pentanol, cyclopentanol, 1-hexanol, cyclohexanol, 1-heptanol, 1-octanol or mixtures thereof. Most preferably the solvent is 1-pentanol.

In another embodiment of either the sixth or seventh aspects of the present invention, from 1 to 100 volumes of the solvent are used, i.e. for every 1 g of erlotinib hydrochloride or erlotinib base respectively, from 1 to 100 ml of solvent are used. Preferably from 5 to 50 volumes of the solvent are used, more preferably from 10 to 30 volumes. Most preferably about 20 volumes of the solvent are used.

Preferably the crystallisation of either the sixth or seventh aspects of the present invention occurs at a temperature of from −10 to 40° C., more preferably from 0 to 30° C., and most preferably from 5 to 10° C.

In another embodiment, the crystallization occurs at a temperature of from 20 to 25° C.

Where erlotinib hydrochloride form A polymorph is isolated in a process according to the present invention, it preferably comprises less than 3% (w/w), more preferably less than 2% (w/w), more preferably less than 1% (w/w), and most preferably less than 0.5% (w/w) of erlotinib hydrochloride in form B or other polymorphic forms.

The extent of form B or other polymorphic forms in the erlotinib hydrochloride form A polymorph may be determined by techniques such as XRPD.

Any erlotinib hydrochloride according to the fifth aspect of the present invention is preferably form A. Preferably the erlotinib hydrochloride form A according to the fifth aspect of the present invention comprises less than 3% (w/w) of erlotinib hydrochloride in form B or other polymorphic forms.

An eighth aspect of the present invention provides erlotinib hydrochloride form A comprising less than 3% (w/w) of erlotinib hydrochloride in form B or other polymorphic forms.

Preferably the erlotinib hydrochloride form A according to the fifth or eighth aspect of the present invention comprises less than 2% (w/w), more preferably less than 1% (w/w), most preferably less than 0.5% (w/w) of erlotinib hydrochloride in form B or other polymorphic forms.

A ninth aspect of the present invention provides erlotinib base, or a salt thereof, prepayable by or when prepared by a process according to any of the first to fourth, sixth or seventh aspects of the present invention.

A tenth aspect of the present invention provides erlotinib base, or a salt thereof, according to any of the fifth, eighth or ninth aspects of the present invention, for use in medicine. For instance, the erlotinib base, or salt thereof, may be used to inhibit protein tyrosine kinases.

An eleventh aspect of the present invention provides a pharmaceutical composition comprising erlotinib base, or a salt thereof, according to any preceding aspect of the present invention or when prepared by a process according to any preceding aspect of the present invention. Preferably the pharmaceutical composition further comprises one or more pharmaceutically acceptable excipients.

Preferably, the pharmaceutical composition according to the eleventh aspect of the present invention comprises a combination with one or more other active ingredients, or is for use in combination with one or more other active ingredients. Preferably, the one or more other active ingredients is an anti cancer drug, preferably gemcitabine.

A twelfth aspect of the present invention provides erlotinib base, or a salt thereof, according to the tenth aspect of the present invention, or a pharmaceutical composition according to the eleventh aspect of the present invention, for use to treat or prevent a disorder wherein inhibiting protein tyrosine kinases is beneficial. Preferably, the disorder is a cancer and more preferably, the cancer is lung cancer or pancreatic cancer.

A thirteenth aspect of the present invention provides a use of erlotinib base, or a salt thereof, according to any of the fifth or eighth to tenth aspects of the present invention, for the manufacture of a medicament for the treatment or prevention of a disorder wherein inhibiting protein tyrosine kinases is beneficial. Preferably, the disorder is a cancer and more preferably, the cancer is lung cancer or pancreatic cancer.

A fourteenth aspect of the present invention provides a method of treating or preventing a disorder wherein inhibiting protein tyrosine kinases is beneficial, comprising administering a therapeutically or prophylactically effective amount of erlotinib base, or a salt thereof, according to any of the fifth or eighth to tenth aspects of the present invention, or of a pharmaceutical composition according to the eleventh aspect of the present invention, to a patient in need thereof. Preferably, the disorder is a cancer and more preferably, the cancer is lung cancer or pancreatic cancer.

In a preferred embodiment of the fourteenth aspect of the present invention, the patient is a mammal. More preferably the patient is a human.

The term "erlotinib" as used herein throughout the description and claims means erlotinib base, i.e. N-(3-ethynylphenyl)-6,7-bis-(2-methoxyethoxy)-4-quinazolinamine, and/or any salt, solvate or polymorph thereof, unless otherwise specified.

Likewise the term "erlotinib base" includes solvates, such as hydrates, and polymorphs thereof, unless otherwise specified. Preferably however, the erlotinib base as referred to herein is anhydrous and/or non-solvated.

Similarly, any "salt of erlotinib" such as erlotinib hydrochloride includes solvates, such as hydrates, and polymorphs thereof, unless otherwise specified. Preferably however, any salt of erlotinib as referred to herein is anhydrous and/or non-solvated.

Unless otherwise specified, the compounds of the present invention can be used both, in their free base form and their acid addition salt form. For the purposes of this invention, a "salt" of a compound of the present invention may be an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic) or amino acids (for example, ornithinic, glutamic or aspartic acid). The acid addition salt may be a mono- or di-acid addition salt. A preferred salt is a hydrohalogenic, sulphuric, phosphoric or organic acid addition salt. A more preferred salt is a hydrochloric acid addition salt.

In addition to pharmaceutically acceptable acid addition salts, other acid addition salts are included in the present invention, since they have potential to serve as intermediates in the purification or preparation of other, for example, pharmaceutically acceptable, acid addition salts, or are useful for identification, characterisation or purification of the free base.

For the purposes of the present invention, the erlotinib or its salts are "substantially pure" if they comprise less than 3% (w/w), preferably less than 2% (w/w), preferably less than 1% (w/w), preferably less than 0.5% (w/w), preferably less than 0.2% (w/w) and most preferably less than 0.1% (w/w) of chemical impurities and/or polymorphic impurities.

For the avoidance of doubt, insofar as is practicable any embodiment of a given aspect of the present invention may occur in combination with any other embodiment of the same aspect of the present invention. In addition, insofar as is practicable it is to be understood that any preferred or optional embodiment of any aspect of the present invention should also be considered as a preferred or optional embodiment of any other aspect of the present invention.

DETAILED DESCRIPTION OF THE INVENTION

Convenient processes for the preparation of chemically pure and polymorphically pure erlotinib and erlotinib salts, such as the hydrochloride salt, have been provided by the present invention. These processes use mild conditions and low temperatures thus minimizing the occurrence of polymorphic inter-conversion and producing erlotinib hydrochloride form A with very high polymorphic purity.

Preferred embodiments of the processes according to the present invention are described in more detail below.

Preferably, the present invention provides processes for the preparation of erlotinib hydrochloride comprising reaction of 4-chloro-6,7-bis-(2-methoxyethoxy)-quinazoline (2) and 3-ethynylaniline (3) in methanol without the use of external acid or base. External acid or base has been used as a catalyst in prior art processes.

The purification of crude erlotinib base (4) is preferably performed by crystallisation from 1-butanol to afford a product with very high yield and purity with an impurity profile well within ICH guidelines.

The purified base (4) is preferably converted into erlotinib hydrochloride (polymorph A) (1) by crystallisation from 1-pentanol and aqueous HCl, or alternatively gaseous HCl dissolved in 1-pentanol.

A preferred embodiment of the present invention is illustrated in Scheme 3.

Another preferred embodiment of the present invention provides a process for the preparation of erlotinib hydrochloride (1) comprising the condensation reaction of 4-chloro-6,7-bis-(2-methoxyethoxy)-quinazoline (2) and 3-ethynylaniline (3) by refluxing in a straight chain, branched or cyclic $C_1$ to $C_6$ alcohol solvent without the use of external acid or acid salt of 3-ethynyl aniline or base.

In another preferred embodiment of the present invention, the crude erlotinib hydrochloride (1) obtained is suspended in a solvent, such as methanol, and treated with a base, such as sodium carbonate, to yield crude erlotinib base (4). If requited, an anti solvent, such as water can be added to precipitate the crude erlotinib base. The erlotinib base is typically isolated by known methods such as filtration or centrifugation.

The base used to isolate the erlotinib base is preferably sodium carbonate but any suitable base may be used as an alternative. Preferred alternative bases are selected from the group consisting of sodium hydroxide, potassium hydroxide, potassium carbonate, ammonia, pyridine and triethylamine.

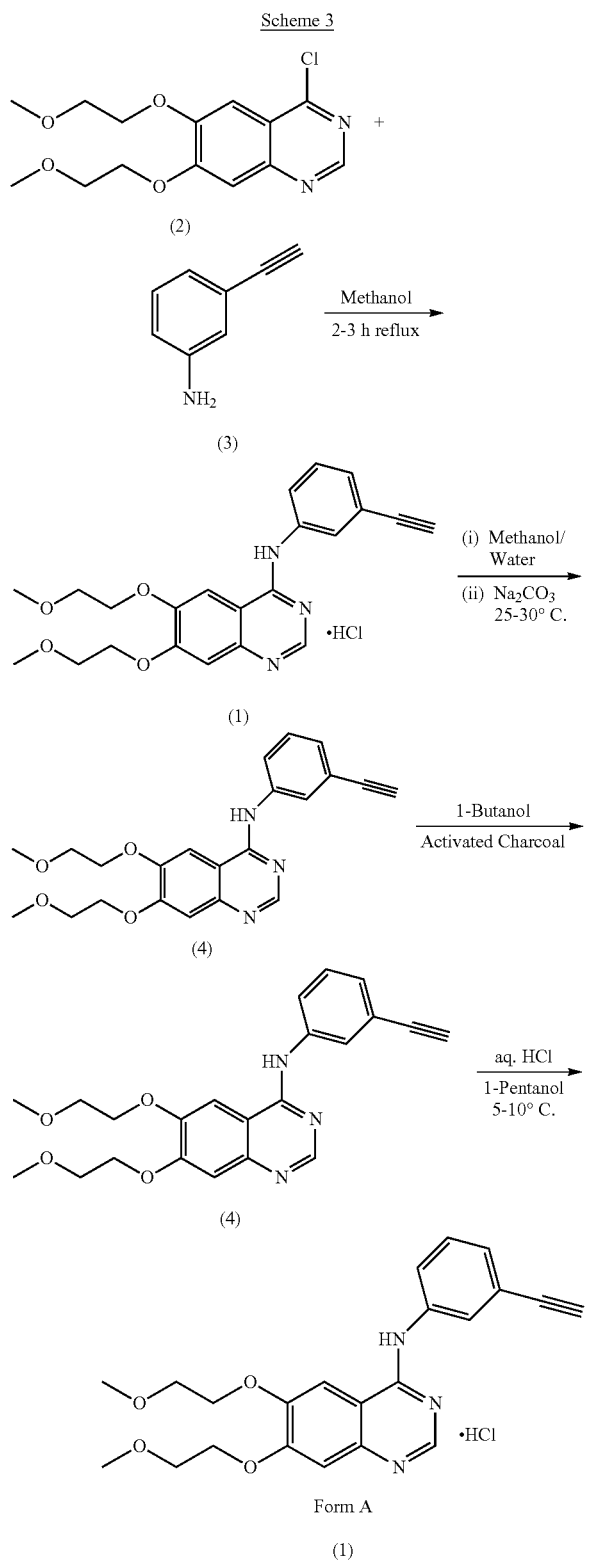

Scheme 3

Preferably, the purification of crude erlotinib base (4) to pure erlotinib base (4) was achieved by crystallization from 1-butanol/activated charcoal. Preferably, the purified erlotinib base is obtained with a HPLC purity >99.9%.

Preferably, the purified erlotinib base obtained has a water content not more than 5% (w/w). The purified erlotinib base may also be dried at 65-75° C. to obtain an anhydrous base.

Preferably, erlotinib hydrochloride polymorph form A is prepared by reaction of the purified erlotinib base (4) in a suitable solvent with aqueous HCl or gaseous HCl. Preferably, the solvent is 1-pentanol. Preferably, the erlotinib hydrochloride is obtained with a HPLC purity >99.9%.

Preferably, the erlotinib hydrochloride obtained was substantially pure and free from polymorph B or other polymorphic forms.

A particularly preferred embodiment of the present invention for the preparation of erlotinib hydrochloride (1) comprises the following steps:
(a) condensation of 4-chloro-6,7-bis-(2-methoxyethoxy) quinazoline (2) and 3-ethynylaniline (3) in an organic reaction solvent to yield crude erlotinib hydrochloride (1);
(b) treatment of the crude erlotinib hydrochloride (1) with base, such as sodium carbonate, to yield crude erlotinib base (4);
(c) crystallisation of the crude erlotinib base (4) from 1-butanol to afford pure erlotinib base (4);
(d) crystallisation of the purified erlotinib base (4) with aqueous HCl in 1-pentanol to afford erlotinib hydrochloride form A.

Preferably, in step (a), the reaction solvent is a straight chain, branched or cyclic $C_1$ to $C_6$ alcohol. Most preferably, the solvent is methanol. Preferably, 5 to 50 volumes, more preferably 20 volumes of solvent are used.

Preferably, the 3-ethynylaniline was added into a solution of 4-chloro-6,7-bis-(2-methoxyethoxy)quinazoline in methanol at 25 to 45° C. and more preferably at 35 to 40° C.

Preferably, after complete addition of 3-ethynylaniline into a solution of 4-chloro-6,7-bis-(2-methoxyethoxy)quinazoline in methanol, the reaction mixture was heated to reflux for 1 to 5 hours, mote preferably 2 to 3 hours.

Preferably, crude erlotinib hydrochloride was isolated by filtration at 25-30° C.

Preferably, the base, such as sodium carbonate, was added between 10 to 40° C. and more preferably between 25 to 30° C.

If required, the volume of anti solvent, such as water added is preferably 5 to 15 volumes, mote preferably 10 volumes.

Preferably, the isolated crude erlotinib base was dried under reduced pressure at 40 to 80° C., more preferably 65-70° C.

Preferably, the dried crude erlotinib base has a water content of not more than 30% (w/w) and mote preferably not more than 10% (w/w) determined by Karl Fischer titration (KF).

The purification of crude erlotinib base is preferably achieved by crystallisation from solvents selected from an alcoholic solvent such as methanol, ethanol, propanol, isopropyl alcohol, butanol and 1-pentanol and most preferably 1-butanol.

Most preferably, the purification of crude erlotinib base was achieved by crystallisation using 6 to 8 volumes of 1-butanol and activated carbon at 75-80° C.

The drying of purified erlotinib base was preferably performed at a temperature ranging from 50 to 100° C. and more preferably 65 to 75° C. under reduced pressure ranging from 600 mm Hg to 50 mm Hg to afford erlotinib base hydrate having a water content of not more than 5% (w/w), as determined by KF.

In another embodiment of the present invention the purified erlotinib base obtained is dried at 65-75° C. to obtain an anhydrous form of erlotinib base with a water content of not more than 0.2% (w/w).

In a preferred aspect of present invention, erlotinib base was converted into erlotinib hydrochloride by using the following sequence:
(i) erlotinib base was added into 1-pentanol;
(ii) aqueous HCl was added;
(iii) the mixture was stirred; and
(iv) the resulting solid was isolated In a preferred embodiment, in step (i), erlotinib base is added into 1-pentanol at a temperature between 0 to 30° C., more preferably at a temperature between 5 to 10° C. Preferably, 1-pentanol is used in the range from 10 to 30 volumes and more preferably 20 volumes.

Preferably, in step (ii), hydrochloric acid was slowly added to a solution at a temperature between 0 to 30° C., more preferably between 5 to 10° C. The hydrochloric acid used is preferably in the form of aqueous hydrochloric acid or in the form of hydrogen chloride gas or hydrogen chloride dissolved in the 1-pentanol. Preferably, the hydrochloric acid was used between 0.25 volumes to 2 volumes of aq. HCl and more preferably 0.5 volumes of aq. HCl. Typically, the concentration of the aq. HCl used was around 35% (w/w). Preferably, after hydrochloric acid addition, the reaction was stirred for at least 1 to 3 hours, more preferably for about 1 hour.

Preferably, the erlotinib hydrochloride was isolated by filtration at a temperature ranging from 0 to 30° C., more preferably between 5 to 10° C.

The white crystalline erlotinib hydrochloride polymorph A obtained had an impurity profile compliant with ICH guidelines. The HPLC purity obtained was preferably more than 99.5%, more preferably more than 99.8% and most preferably more than 99.9%.

The erlotinib hydrochloride, crystalline polymorph form A, was characterized by XRPD. The XRPD pattern and 2θ values are in good agreement with the form A characterised in the prior art (e.g. in document WO 01/34574), although the form A of the present invention is more pure.

The pharmaceutical composition according to the present invention can be a solution or a suspension but is preferably a solid oral dosage form. Preferred oral dosage forms in accordance with the invention include tablets, capsules and the like which, optionally, may be coated if desired. Tablets can be prepared by conventional techniques, including direct compression, wet granulation and dry granulation. Capsules are generally formed from a gelatine material and can include a conventionally prepared granulate of excipients in accordance with the invention.

The pharmaceutical composition according to the present invention typically comprises one or more conventional pharmaceutically acceptable excipient(s) selected from the group comprising of a filler, a binder, a disintegrant, a lubricant and optionally further comprises at least one excipient selected from colouring agents, adsorbents, surfactants, film formers and plasticizers.

If the solid pharmaceutical formulation is in the form of coated tablets, the coating may be prepared from at least one film-former such as hydroxypropyl methylcellulose, hydroxypropyl cellulose or methacrylate polymers which optionally may contain at least from one plasticizer such as polyethylene glycols, dibutyl sebacate, triethyl citrate, and other pharmaceutical auxiliary substances conventional for film coatings, such as pigments and fillers.

Preferably the pharmaceutical compositions according to the present invention are in unit dosage form comprising erlotinib in an amount of from 1 mg to 500 mg, such that the amount of erlotinib administered is from 0.1 mg to 100 mg per Kg per day.

The details of the invention, its objects and advantages are illustrated below in greater detail by non-limiting examples.

EXAMPLES

Example 1

Preparation of Crude Erlotinib Base 4-chloro-6,7-bis-(2-methoxyethoxy)quinazoline (50 g, 0.1598 mol) was added to methanol (900 ml, 18 vol.) and the mixture was heated to 35-40° C. to obtain a uniform suspension. 3-Ethynylaniline (20.6 g, 0.1758 mol) was mixed with 100 ml (2 vol.) of methanol and added drop wise into the uniform suspension of 4-chloro-6,7-bis-(2-methoxyethoxy) quinazoline over a period of 15 min at 35-40° C. The temperature of the reaction mixture was slowly raised to 60-65° C. and maintained for 2-3 hours. The reaction was monitored by TLC as well as HPLC. When the 4-chloro-6,7-bis-(2-methoxyethoxy)-quinazoline content in the reaction mixture was not more than 3%, the reaction mixture was cooled to 25-30° C. and crude erlotinib hydrochloride was isolated by filtration. The cake was washed with 100 ml (2 vol.) of methanol and suck dried.

The wet cake of crude erlotinib hydrochloride was added to 500 ml (10 vol.) of methanol under stirring at 25-30° C. to obtain a suspension. Sodium carbonate (33.8 g, 0.3197 mol) was added to the mixture at 25-30° C. and stirred for one hour at 25-30° C. 500 ml (10 vol.) of water was added to the reaction mixture and stirred for one hour. The crude erlotinib base was isolated by filtration and suck dried before adding it to 250 ml (5 vol.) of water at 25-30° C. and stirred for 30 min. The erlotinib base was isolated by filtration and washed with 50 ml (1 vol.) of water and suck dried to get 70 g as a wet cake. This wet cake was dried under reduced pressure at 100 mm Hg for 3 hour at 60-65° C. to afford 63 g of erlotinib base as an off-white powder.

Molar yield=100%
HPLC purity >99%.

Example 2

Further Purification of Crude Erlotinib Base 60 g of crude erlotinib base was added to 480 ml (8 vol.) of 1-butanol under stirring at 25-30° C. The mixture was heated to 80-85° C. to obtain a clear solution and maintained for one hour at 80-90° C. The solution was slowly cooled to 25-30° C. and the product was isolated by filtration and washed with 120 ml (2 vol.) of 1-butanol. The wet cake was again added to 360 ml (6 vol.) of 1-butanol and the mixture heated to 80-90° C. to obtain a clear solution. 2.7 g Activated charcoal (Norit B) was added into the clear solution and maintained for 1 hour at 80-85° C. The reaction mixture was filtered through a Celite bed at 80-85° C. and the Celite bed was washed with 1 volume hot 1-butanol. The combined mother liquor was slowly cooled to 25-30° C. and stirred for 1 hour. The product was isolated by filtration and washed with 120 ml (2 vol.) of 1-butanol. The purified erlotinib base was dried at 65-75° C. for 8 hours, under reduced pressure (160 mm Hg) to afford 35 g as a white powder.

Molar yield=58.3%
HPLC purity 99.9%

Example 3

Preparation of Erlotinib Hydrochloride Polymorph Form A 115 g (0.292 mol) of erlotinib base was added to 2300 ml (20 vol) of 1-pentanol at 25-30° C. The mixture was cooled to 5 to 10° C. and stirred for 30 min. to obtain a suspension. 57.5 g of aqueous hydrochloric acid at a concentration of 35% (w/w) was added drop wise at 5-10° C. and the mixture stirred for 1 hour. The product was isolated by filtration and washed with 230 ml (2 vol.) of 1-pentanol. The product was dried under reduced pressure (50 mm Hg) at 0-60° C. to obtain 113 g of erlotinib hydrochloride polymorph A as a white solid.

Molar yield=90%
HPLC purity 99.85%

No polymorphic form B or any other polymorphic form could be detected in the product by XRPD. (Limit of detection 0.2% (w/w); limit of quantification 0.4% (w/w)).

Example 4

Alternative Preparation of Erlotinib Hydrochloride Polymorph Form A

In a 2.0 liter, 4 neck, round bottom flask equipped with a mechanical stirrer, a thermometer pocket and a reflux condenser, 420 ml of 1-pentanol (16.8 volumes with respect to erlotinib base) and 25 g (0.0635 mol) of N-(3-ethynylphenyl)-6,7-bis(2-methoxyethoxy)-4-quinazolinamine (erlotinib base) was charged at 25-30° C. under stirring. The reaction mixture was then cooled to 20-25° C. to obtain a suspension. 30 ml of 1-pentanol-HCl solution (prepared by scrubbing HCl gas into 1-pentanol to a concentration by assay of 16-18% (w/w)) was added drop wise over a period of 15 minutes at a temperature of 20-25° C. The reaction mixture was stirred for a further 1 hour. The product was isolated by filtration, washed with 25 ml of 1-pentanol, and dried under reduced pressure (50 mm Hg) at 50-55° C., to give 25 g of erlotinib hydrochloride polymorph A (loss on drying <0.5%).

Molar yield=91.5%
HPLC purity >99.8%

No polymorphic form B or any other polymorphic form could be detected in the product by XRPD. (Limit of detection 0.2% (w/w); limit of quantification 0.4% (w/w)).

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A process for the preparation of erlotinib base, comprising crystallizing erlotinib base from a solvent comprising a straight chain, branched, or cyclic C4 to C20 alcohol, wherein the erlotinib base is dissolved in the solvent and treated with activated charcoal, prior to crystallisation from the solvent.

2. The process according to claim 1, wherein the solvent is:
(a) a straight chain, branched or cyclic C4 to C12 alcohol; or
(b) a straight chain, branched or cyclic C4 to C8 alcohol; or
(c) 1-butanol, 2-methyl-1-propanol, t-butanol, 1-pentanol, cyclopentanol, 1-hexanol, cyclohexanol, 1-heptanol or 1-octanol; or
(d) 1-butanol.

3. The process according to claim 1, wherein the crystallizing is performed by heating the erlotinib base in the solvent at a first temperature until the erlotinib base has dissolved, and then cooling the solution to a second temperature to allow the erlotinib base to crystallize.

4. The process according to claim 1, wherein the first temperature is:
(a) from 60° C. to 100° C.; or
(b) from 80° C. to 90° C.

5. The process according to claim 1, wherein the second temperature is:
(a) from −10° C. to 40° C.; or
(b) from 25° C. to 30° C.

6. The process according to claim 1, wherein:
(a) between 1 and 20 volumes of solvent are used for the crystallizing; or
(b) between 3 and 15 volumes of solvent are used for the crystallizing; or
(c) between 6 and 8 volumes of solvent are used for the crystallizing.

7. The process according to claim 1, wherein the erlotinib base is prepared by reacting 4-chloro-6,7-bis-(2-methoxyethoxy)quinazoline and 3-ethynylaniline in a reaction solvent, wherein the reaction mixture does not contain an external acid or base.

8. The process according to claim 1, wherein the erlotinib base is prepared by reacting 4-chloro-6,7-bis-(2-methoxyethoxy)quinazoline and 3-ethynylaniline in a reaction solvent, wherein the reaction mixture does not contain an external acid or base, to yield a salt of erlotinib; and
treating the salt of erlotinib with a base to yield erlotinib base.

9. The process according to claim 1, wherein the erlotinib base is prepared by reacting a salt of erlotinib with a base in a solvent consisting of:
(a) methanol and optional water; or
(b) ethanol and optional water; or
(c) methanol and ethanol and optional water.

10. The process according to claim 1, wherein the erlotinib base is prepared by reacting a salt of erlotinib with a carbonate or bicarbonate base in a solvent consisting of one or more polar protic solvents.

11. A process for the preparation of erlotinib hydrochloride form A, comprising dissolving erlotinib base in a solvent, mixing with aqueous or non-aqueous HCl and crystallizing erlotinib hydrochloride from the solvent, wherein the erlotinib base is prepared by a process according to claim 1.

12. Erlotinib base with a HPLC purity of more than 99.8%.

13. Erlotinib base according to claim 12, with a HPLC purity of more than 99.9%.

14. A pharmaceutical composition comprising erlotinib base according to claim claim 12.

15. The pharmaceutical composition according to claim 14:
(a) further comprising one or more other active ingredients; or
(b) further comprising one or more anti-cancer drugs.

16. A method of treating lung cancer or pancreatic cancer comprising administering a therapeutically effective amount of erlotinib base according to claim 12 to a patient in need thereof.

17. A method of treating lung cancer or pancreatic cancer comprising administering a therapeutically effective amount of a pharmaceutical composition according to claim 14 to a patient in need thereof.

18. The pharmaceutical composition according to claim 14 further comprising gemcitabine.

\* \* \* \* \*